United States Patent
Govari et al.

(10) Patent No.: US 11,937,780 B2
(45) Date of Patent: Mar. 26, 2024

(54) SINGLE HANDED ENT TOOL

(71) Applicant: BIOSENSE WEBSTER (ISRAEL) LTD., Yokneam (IL)

(72) Inventors: Assaf Govari, Haifa (IL); Yehuda Algawi, Binyamina (IL); Ilya Sitnitsky, Nahariya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 673 days.

(21) Appl. No.: 17/064,262

(22) Filed: Oct. 6, 2020

(65) Prior Publication Data

US 2021/0015344 A1 Jan. 21, 2021

Related U.S. Application Data

(63) Continuation of application No. 16/101,502, filed on Aug. 12, 2018, now abandoned.

(Continued)

(51) Int. Cl.
*A61B 1/233* (2006.01)
*A61B 1/00* (2006.01)
(Continued)

(52) U.S. Cl.
CPC ........ *A61B 1/0052* (2013.01); *A61B 1/00066* (2013.01); *A61B 1/233* (2013.01);
(Continued)

(58) Field of Classification Search
CPC ................ A61B 1/0052; A61B 1/0053; A61B 1/00066; A61B 1/233; A61B 1/273;
(Continued)

(56) References Cited

U.S. PATENT DOCUMENTS 3,986,031 A * 10/1976 Chekroun .............. A61B 6/025
378/11
4,230,949 A * 10/1980 Distler ................... A61B 6/035
378/10

(Continued)

FOREIGN PATENT DOCUMENTS

EP 3437573 2/2019

OTHER PUBLICATIONS

European Search Report dated Jul. 24, 2020 from corresponding European Patent Application No. 20170881.5.
European Search Report dated Dec. 20, 2018 from corresponding European Patent Application No. 18192645.2.
U.S. Appl. No. 15/155,850, filed May 16, 2016.

*Primary Examiner* — Tan-Uyen T Ho
*Assistant Examiner* — Bridget E. Rabaglia

(57) ABSTRACT

A tool, consisting of an enclosure and a rotatable knob retained by, and protruding from, the enclosure. The tool has a tube having a proximal end that is retained by the enclosure, and the tube has an axis of symmetry. A Geneva drive is retained within the enclosure, the Geneva drive consisting of a drive wheel fixedly attached to the rotatable knob and a driven wheel fixedly attached to the proximal end of the tube, so that an axis of rotation of the driven wheel coincides with the axis of symmetry of the tube. Thus, a continuous rotation of the rotatable knob causes the tube to rotate about the axis of symmetry in discrete angular steps.

7 Claims, 11 Drawing Sheets

Related U.S. Application Data

(60) Provisional application No. 62/554,894, filed on Sep. 6, 2017.

(51) Int. Cl.

| | | |
|---|---|---|
| *A61B 1/005* | (2006.01) | |
| *A61B 1/273* | (2006.01) | |
| *A61B 17/24* | (2006.01) | |
| *A61B 34/20* | (2016.01) | |
| *F16H 27/06* | (2006.01) | |
| *A61B 17/00* | (2006.01) | |
| *A61B 17/17* | (2006.01) | |
| *A61B 17/22* | (2006.01) | |
| *A61B 17/29* | (2006.01) | |
| *A61B 17/34* | (2006.01) | |
| *A61B 90/00* | (2016.01) | |

(52) U.S. Cl.
CPC ............. *A61B 17/24* (2013.01); *F16H 27/06* (2013.01); *A61B 1/273* (2013.01); *A61B 2017/003* (2013.01); *A61B 17/1771* (2016.11); *A61B 17/1785* (2016.11); *A61B 2017/22038* (2013.01); *A61B 2017/2929* (2013.01); *A61B 17/3421* (2013.01); *A61B 2034/2051* (2016.02); *A61B 2090/3954* (2016.02)

(58) Field of Classification Search
CPC ............... A61B 17/24; A61B 17/3421; A61B 2017/003; A61B 2034/2051; A61B 2090/3954; A61B 2017/22051; A61B 2017/22038; A61B 17/1785; F16H 27/06
See application file for complete search history.

(56) References Cited

U.S. PATENT DOCUMENTS

| | | | | |
|---|---|---|---|---|
| 5,281,984 | A * | 1/1994 | Burton | A61B 3/0285 351/221 |
| 5,381,943 | A * | 1/1995 | Allen | A61B 17/0682 227/19 |
| 2008/0195066 | A1* | 8/2008 | Speeg | A61B 10/0275 604/326 |
| 2008/0200836 | A1* | 8/2008 | Speeg | A61B 10/0266 600/567 |
| 2008/0214955 | A1* | 9/2008 | Speeg | A61B 10/0275 600/567 |
| 2008/0228103 | A1* | 9/2008 | Ritchie | A61B 10/0275 600/565 |
| 2009/0073382 | A1* | 3/2009 | Bischoff | G02B 27/123 351/211 |
| 2012/0022635 | A1* | 1/2012 | Yamashita | A61F 2/95 623/1.12 |
| 2014/0140471 | A1* | 5/2014 | Tybinkowski | A61B 6/032 378/19 |
| 2014/0303623 | A1* | 10/2014 | Diehl | A61F 2/4644 606/79 |
| 2014/0323993 | A1 | 10/2014 | Wilcox et al. | |
| 2015/0080911 | A1* | 3/2015 | Reed | A61B 17/068 606/139 |
| 2016/0089121 | A1 | 3/2016 | Stand et al. | |
| 2016/0184097 | A1* | 6/2016 | Lim | A61F 2/2439 623/2.11 |
| 2016/0270871 | A1* | 9/2016 | Takei | A61B 34/71 |
| 2017/0056043 | A1 | 3/2017 | Jenkins et al. | |
| 2017/0120019 | A1* | 5/2017 | Goldfard | A61M 25/09041 |
| 2017/0128661 | A1 | 5/2017 | Chow et al. | |
| 2017/0265584 | A1* | 9/2017 | Walker | G01L 1/12 |
| 2019/0298945 | A1* | 10/2019 | Akouka | A61M 15/0021 |

OTHER PUBLICATIONS

\* cited by examiner

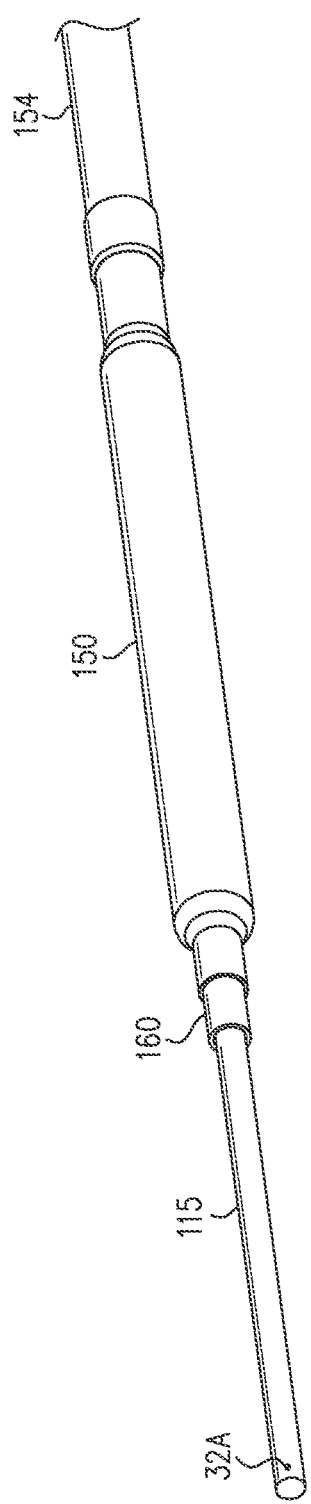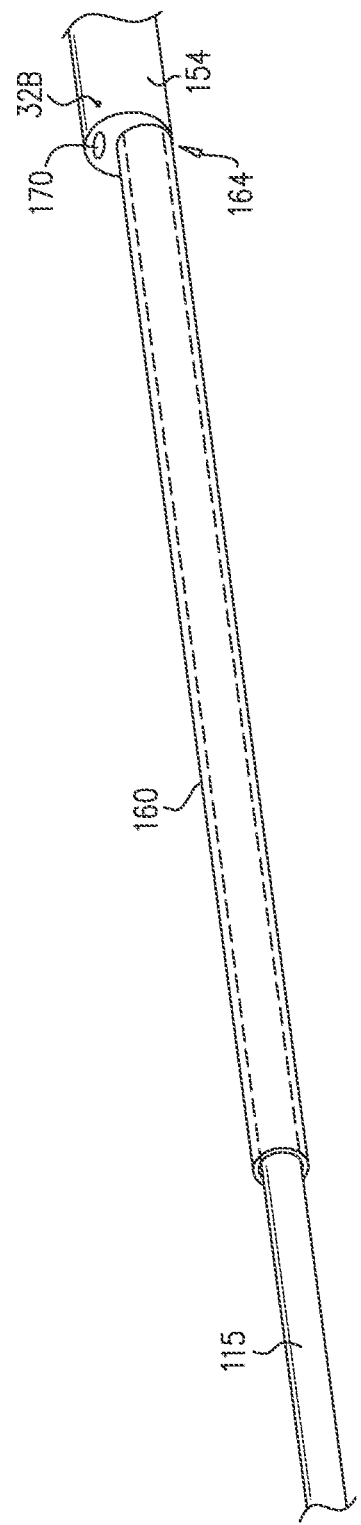

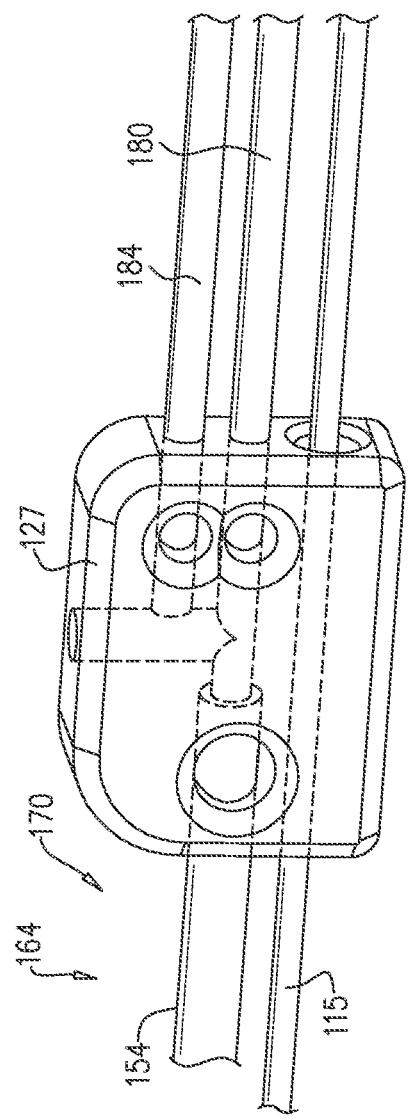

SINGLE HANDED ENT TOOL

CROSS REFERENCE TO RELATED APPLICATION

This application is a continuation of U.S. patent application Ser. No. 16/101,502, filed Aug. 12, 2018, which claims the benefit of U.S. Provisional Patent Application 62/554,894, filed Sep. 6, 2017.

FIELD OF THE INVENTION

This invention relates generally to surgical tools, and specifically to a surgical tool used for ENT (ear, nose, and throat) procedures.

BACKGROUND OF THE INVENTION

In an ENT procedure involving the sinuses, the configuration of the sinuses typically restricts the freedom of movement of an ENT tool used to inspect or to operate in the sinuses. A physician may at least partially overcome the restriction by using both of his/her hands, but this requirement may be undesirable to the physician.

SUMMARY OF THE INVENTION

An embodiment of the present invention provides a tool, including:
an enclosure;
a rotatable knob retained by, and protruding from, the enclosure;
a tube having a proximal end retained by the enclosure, the tube having an axis of symmetry; and
a Geneva drive retained within the enclosure, the Geneva drive consisting of a drive wheel fixedly attached to the rotatable knob and a driven wheel fixedly attached to the proximal end of the tube, so that an axis of rotation of the driven wheel coincides with the axis of symmetry of the tube,
whereby a continuous rotation of the rotatable knob causes the tube to rotate about the axis of symmetry in discrete angular steps.

In a disclosed embodiment the Geneva drive has eight different fixed positions.

In a further disclosed embodiment the tube has a distal end having dimensions enabling it to be inserted into an orifice of a human patient. The orifice may be a nasal sinus.

There is further provide, according to an embodiment of the present invention, a method, including:
providing an enclosure;
positioning a rotatable knob to be retained by, and protrude from, the enclosure;
positioning a tube having a proximal end to be retained by the enclosure, the tube having an axis of symmetry; and
positioning a Geneva drive to be retained within the enclosure, the Geneva drive consisting of a drive wheel fixedly attached to the rotatable knob and a driven wheel fixedly attached to the proximal end of the tube, so that an axis of rotation of the driven wheel coincides with the axis of symmetry of the tube,
whereby a continuous rotation of the rotatable knob causes the tube to rotate about the axis of symmetry in discrete angular steps.

The present disclosure will be more fully understood from the following detailed description of the embodiments thereof, taken together with the drawings, in which:

BRIEF DESCRIPTION OF THE DRAWINGS

FIG. 10 and FIG. 11 are schematic illustrations of portions of a guidewire and a balloon insertion mechanism, according to an embodiment of the present invention;

FIG. 12 is a schematic transparent view of a manifold, according to an embodiment of the present invention.

DETAILED DESCRIPTION OF EMBODIMENTS

Overview

Figure 1:
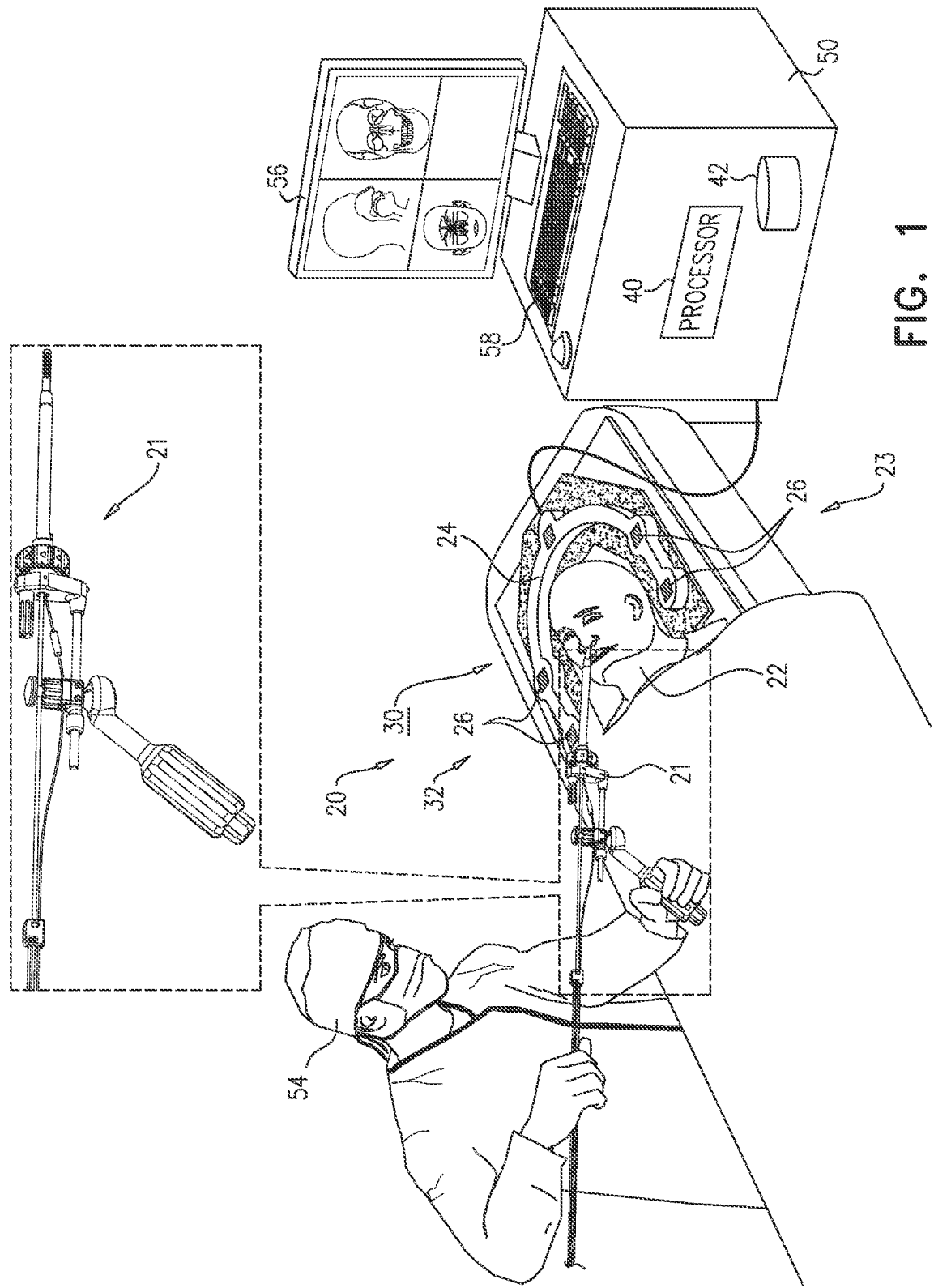
FIG. 1 is a schematic illustration of an ENT (ear, nose, and throat) system, according to an embodiment of the present invention.

An embodiment of the present invention provides a physician performing an ENT (ear nose and throat) procedure with a balloon sinuplasty tool that can be held by one hand, and wherein some of the functions of the tool can be implemented by the fingers of the hand. Specifically, while holding the tool, the physician is able to deflect the distal tip of the tool end away from the tool end axis, and independently rotate the tool end around its axis. The deflection and the rotation can be performed by the fingers of the hand holding the tool.

In one embodiment of the present invention the tool comprises an enclosure which retains a rotatable knob, so that the knob protrudes from the enclosure. The tool also comprises a tube that has an axis of symmetry, and that has a proximal end retained by the enclosure. A distal end of the tube has dimensions enabling it to be inserted into an orifice of a patient.

The enclosure of the tool contains a Geneva drive, which is connected so that a drive wheel is fixedly attached to the rotatable knob. In addition, a driven wheel of the Geneva drive is fixedly attached to the tube proximal end so that an axis of rotation of the driven wheel coincides with the tube axis of symmetry.

The Geneva drive enables the tube to be rotated, by continuous rotation of the rotatable knob, by discrete angular steps into a number of discrete positions. In each of these positions, even though the knob may continue to be rotated, the Geneva drive locks the tube in place so that it does not rotate. While in any one of these discrete positions, other operations may be performed on the tube, such as deflection of the distal tip from the tool end axis, and the possibility of performing such multiple operations simultaneously and independently significantly assists the physician during a procedure.

The tool also comprises a guidewire insertion mechanism, and a balloon insertion mechanism. The guidewire and the balloon (of their respective mechanisms) can be independently threaded through the tool end, and functions of the mechanisms can also be independently implemented. The guidewire comprises a location sensor at its distal tip and typically the physician may be able to deflect the guidewire tip.

Typically, after the physician has manipulated the tool end to enable access to a desired sinus region, the guidewire is threaded through the tool end, and is manipulated until it is at or beyond the region. The balloon is then pushed along the guidewire to the region, at which point it may be inflated to perform sinuplasty.

In addition to the functions listed above, the tool provides channels for suction from the distal end, for the inflation of the balloon, and for irrigation at the distal end.

By incorporating all the above functions into one tool, and by enabling manipulation of the tool end to be implemented by the one hand holding the tool, the physician performing the procedure has substantially more freedom of movement than in prior art systems.

DETAILED DESCRIPTION

Reference is now made to FIG. 1, which is a schematic illustration of an ENT (ear, nose, and throat) system 20, according to an embodiment of the present invention. In the following description a single-handed ENT tool 21 in system is assumed to be used to perform a balloon sinuplasty procedure on a patient 22 so that a distal end of the tool is assumed to have dimensions permitting entry to a nasal sinus of the patient. However, it will be understood that the tool may be used to perform other procedures on the patient.

Tool 21 comprises one or more magnetic sensors 32A, 32B, . . . , generically termed sensors 32, which are typically single axis coils or a triple axis coils, that are tracked during the procedure by a magnetic tracking system 23. For the tracking to be effective, in system 20 frames of reference of a CT (computerized tomography) image of patient 22 and of magnetic tracking system 23, are registered. While the CT image may typically comprise a magnetic resonance imaging (MRI) image or a fluoroscopic image, in the description herein the image is assumed to comprise, by way of example, a fluoroscopic CT image.

Prior to and during the sinus procedure, a magnetic radiator assembly 24, comprised in the magnetic tracking system, is positioned beneath the patient's head. Assembly 24 comprises magnetic field radiators 26 which are fixed in position and which transmit alternating magnetic fields into a region 30 wherein the head of patient 22 is located. Potentials generated by a magnetic sensor such as a given sensor 32 in region 30, in response to the magnetic fields, enable the position and the orientation of the sensor to be measured in the magnetic tracking system's frame of reference.

By way of example, radiators 26 of assembly 24 are arranged in an approximately horseshoe shape around the head of patient 22. However, alternate configurations for the radiators of assembly 24 will be apparent to those having ordinary skill in the art, and all such configurations are assumed to be comprised within the scope of the present invention.

Prior to the procedure, the registration of the frames of reference of the magnetic tracking system with the CT image may be performed by positioning a magnetic sensor at known positions, such as the tip of the patient's nose, of the image. However, any other convenient system for registration of the frames of reference may be used.

Elements of system 20, including radiators 26 and sensors 32, are under overall control of a system processor 40. Processor 40 may be mounted in a console 50, which comprises operating controls 58 that typically include a keypad and/or a pointing device such as a mouse or trackball. Console 50 connects to the radiators and to sensors 32 via one or more cables cable and/or wirelessly. A physician 54 uses operating controls 58 to interact with the processor while performing the ENT procedure using system 20. While performing the procedure, the processor may present results of the procedure on a screen 56.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Figure 2:
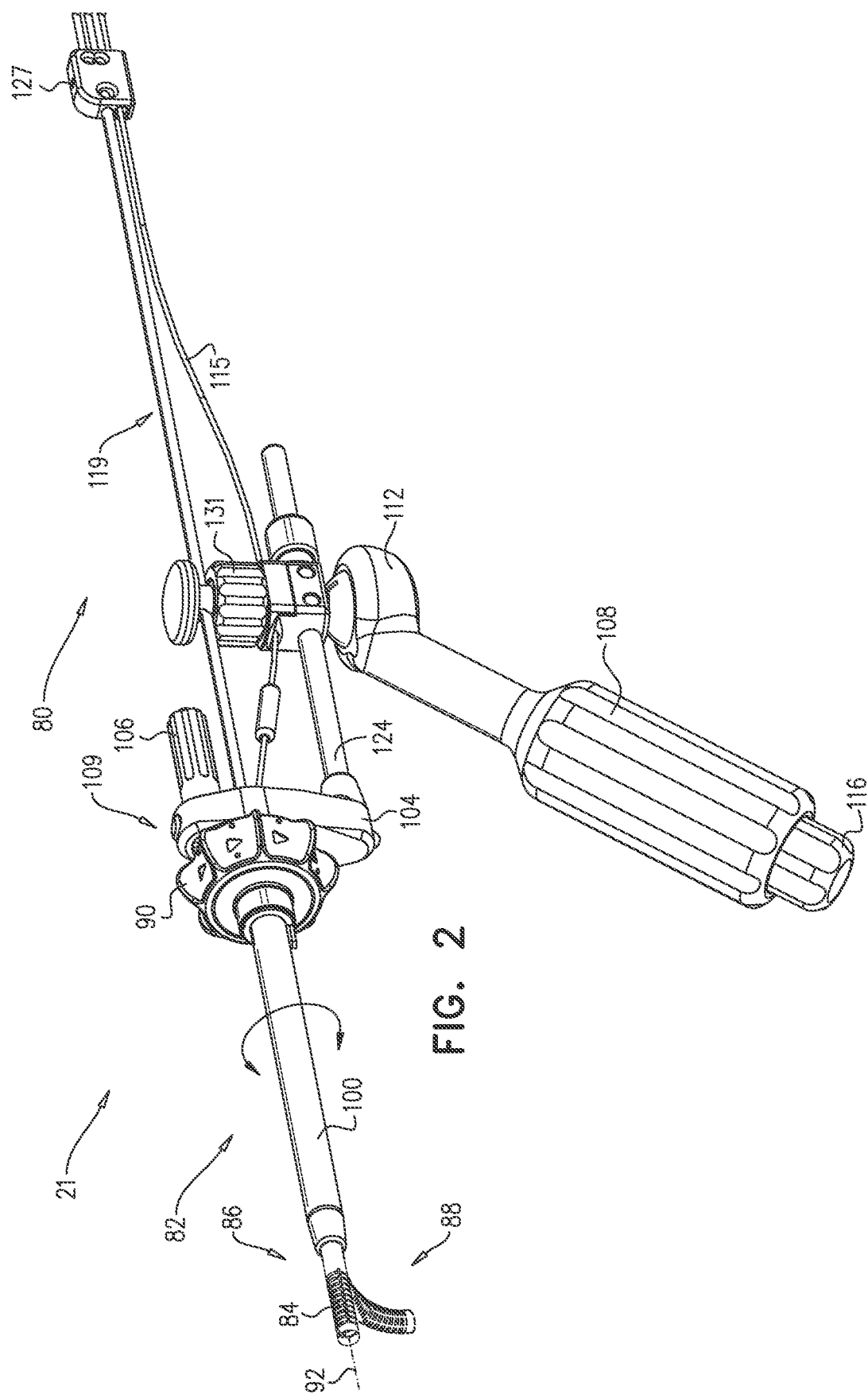
FIG. 2 is a schematic diagram of an ENT tool, according to an embodiment of the present invention.

FIG. 2 is a schematic diagram of tool 21, according to an embodiment of the present invention. Tool 21 comprises a proximal section 80 and a distal section 82 which are connected together, but the distal section may be disassembled and removed from the proximal section. In some embodiments the proximal and/or distal sections are designed to be disposable, typically after one procedure has been performed.

At its distal end distal section 82 comprises an articulated tubular section 84, which may be adjustably bent from a straight configuration 86 to a curved configuration 88, the latter being schematically shown in the diagram by broken lines. In the straight configuration tubular section 84 defines an axis of symmetry 92, which is also an axis of symmetry of a tube 100 to which section 84 is connected, as described below. The adjustment from the straight to the curved configuration, and vice versa, may be performed by clockwise and counter-clockwise rotation of a ribbed knob 90, the construction and function of which, and of entities connected to it, are described further below with respect to FIGS. 4 and 5. U.S. patent application Ser. No. 15/155,850, filed May 16, 2016, titled "Insertion Tube with Deflectable Tip," which is incorporated herein by reference, describes the construction and operation of a deflectable articulated section such as section 84.

Tubular section 84 is fixedly connected at its proximal end to tube 100 which may be rotated about axis of symmetry 92, as indicated by the double headed arrow in the figure. The rotation of tube 100 may be implemented by rotating a ridged knob 106, the knob in turn being connected to a rotation system 109 housed in a rotation system enclosure 104. Rotation system 109 is described below with respect to FIGS. 6, 7, 8 and 9.

Tool 21 comprises a handle 108 which connects to the tool by a ball-joint 112. The physician holding the tool is able to adjust the handle's position according to the physician's preference, and then to lock the handle against the ball-joint by turning a locking knob 116 on the handle.

Tube 100 and articulated section 84 comprise a central lumen which permits the passage of a guidewire 115 and a balloon insertion mechanism 119, from proximal section 80, through the lumen. The guidewire and the mechanism are described further below, with respect to FIGS. 10 and 11. Proximal sections of the guidewire and the insertion mechanism are held in place by a manifold 127, which is described with respect to FIG. 12, and the sections may be locked in place, as required, by a locking mechanism 131 which is described with respect to FIG. 13.

Figure 3:
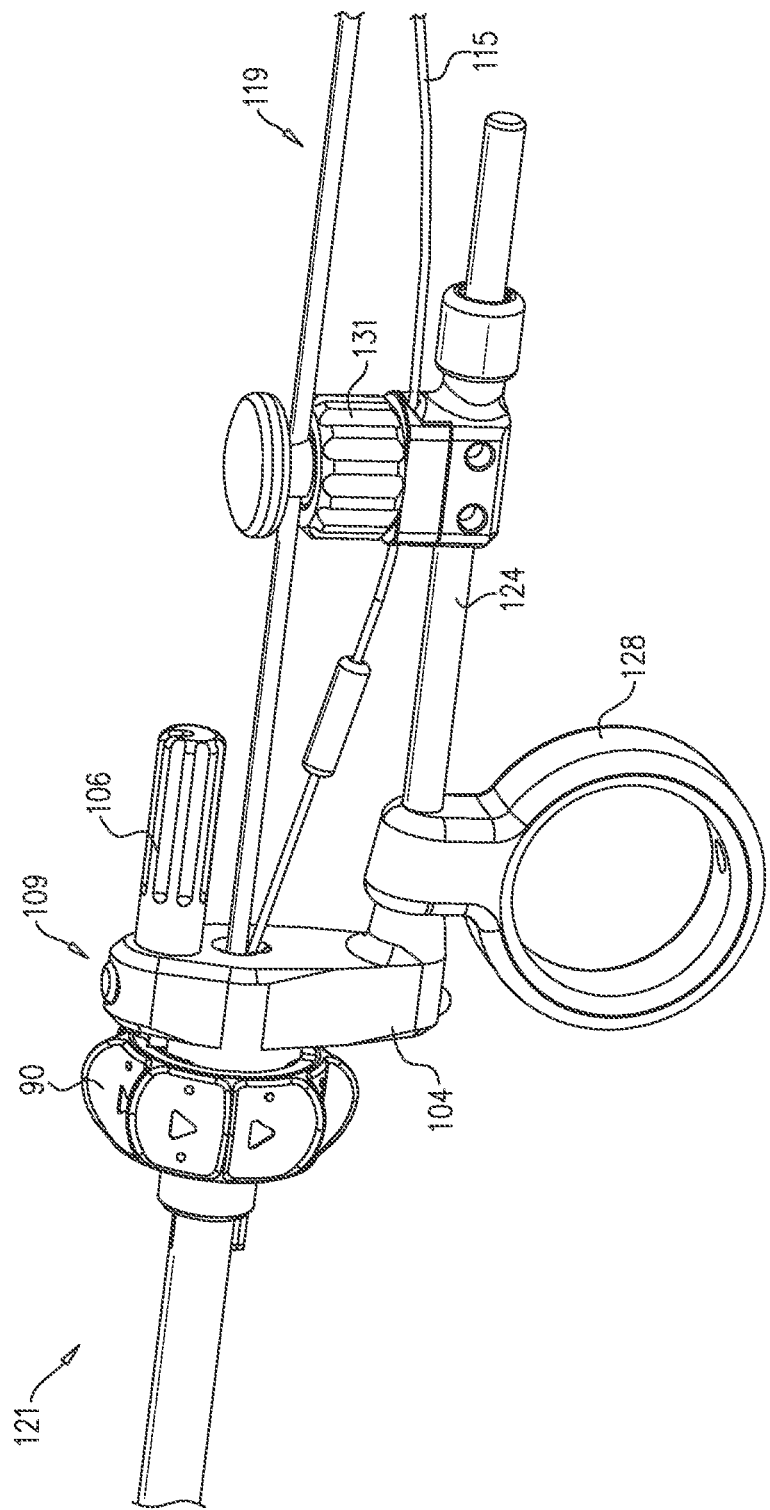
FIG. 3 is a schematic diagram of an ENT tool, according to an alternative embodiment of the present invention.

FIG. 3 is a schematic diagram of a tool 121, according to an alternative embodiment of the present invention. Apart from the differences described below, the operation of tool 121 is generally similar to that of tool 21 and elements indicated by the same reference numerals in both 21 and 121 are generally similar in construction and in operation.

Tool 121 comprises, in place of handle 108, a ring element 128 which connects to a suction tube 124 (described below). The physician using tool 121 is able to use his/her finger or thumb to hold element 128, and thus hold the tool.

For simplicity and clarity, the remainder of the present application assumes tool 21 is used, and those having ordinary skill in the art will be able to adapt the description, mutatis mutandis, if tool 121 is used.

Figure 5:
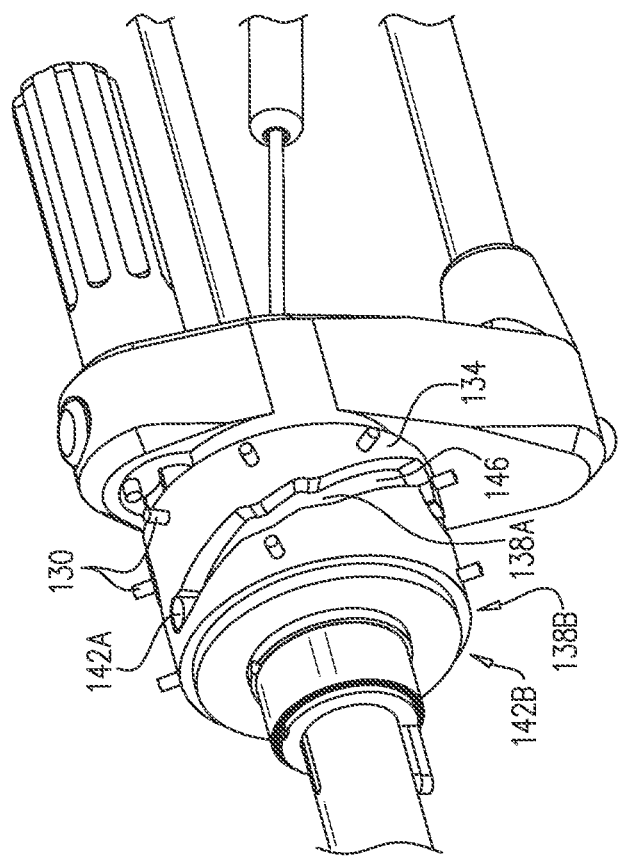
FIGS. 4 and 5 are schematic detail figures of a knob and its internal construction, according to an embodiment of the present invention.
Figure 4:
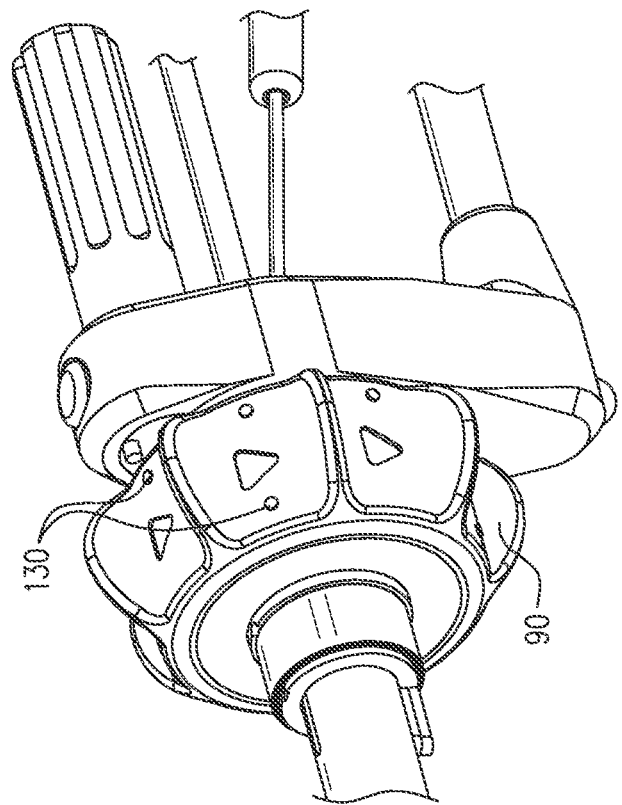

FIGS. 4 and 5 are schematic detail figures of knob 90 and its internal construction, according to an embodiment of the present invention. Knob 90, which is hidden in FIG. 5, is rigidly connected by pins 130 to a cylinder 134, and the cylinder comprises a first groove 138A and a second groove 138B at 180° to the first groove, the two grooves being configured as a double-start screw thread. A first pin 142A and a second pin 142B at 180° to the first pin are mounted on an internal cylinder 146 so that pin 142A resides within groove 138A and pin 142B resides within groove 138B. Rotation of knob 90 thus causes the knob and cylinder 134 to move in a forward or backward motion parallel to axis 92. Cylinder 134 is coupled by an internal element to wires (the internal element and the wires are not shown in the figures) connected to distal section 84, so that the motion of the cylinder parallel to axis 92 causes the distal section to bend to curved configuration 88 or straighten to straight configuration 86.

Figure 6:
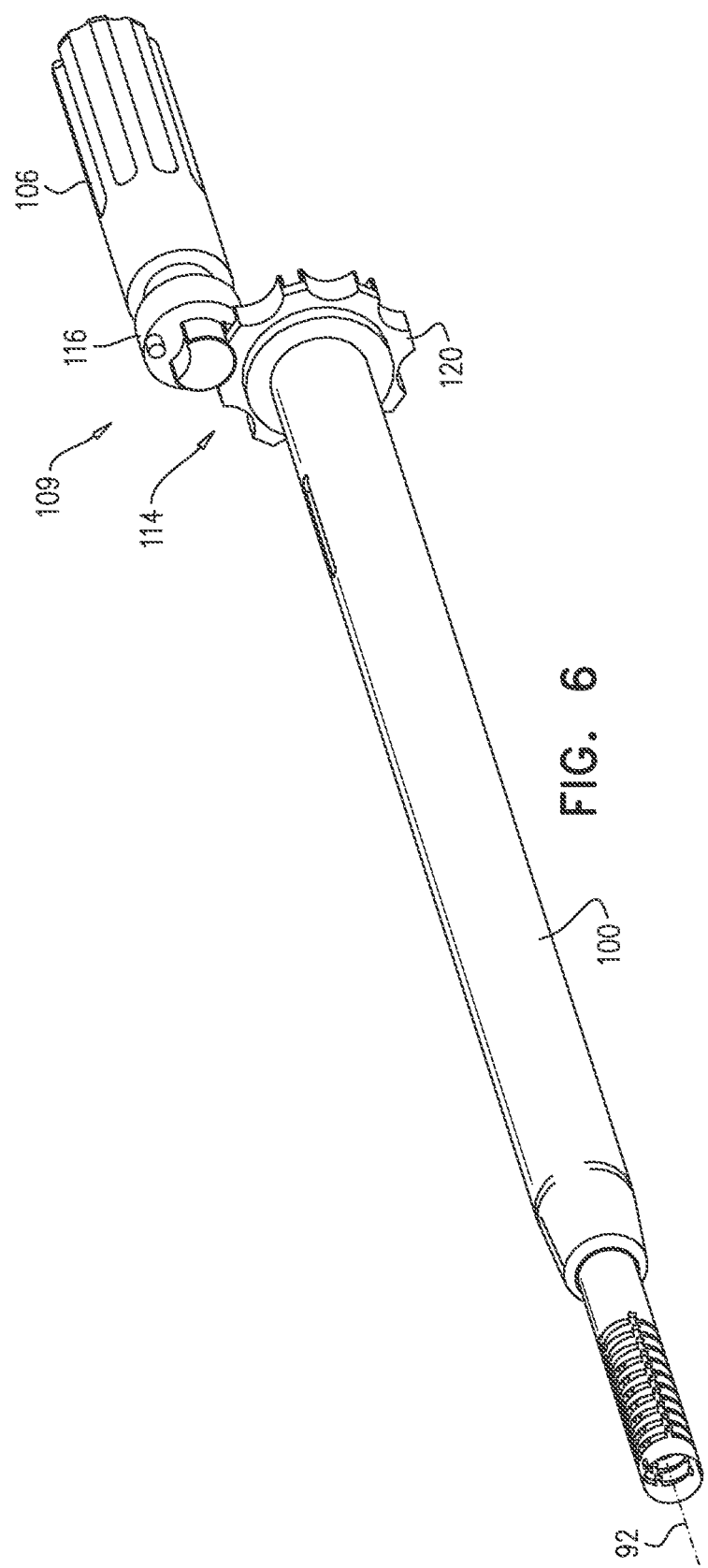
FIGS. 6, 7, 8, and 9 are schematic figures illustrating a rotation system, according to an embodiment of the present invention.
Figure 7:
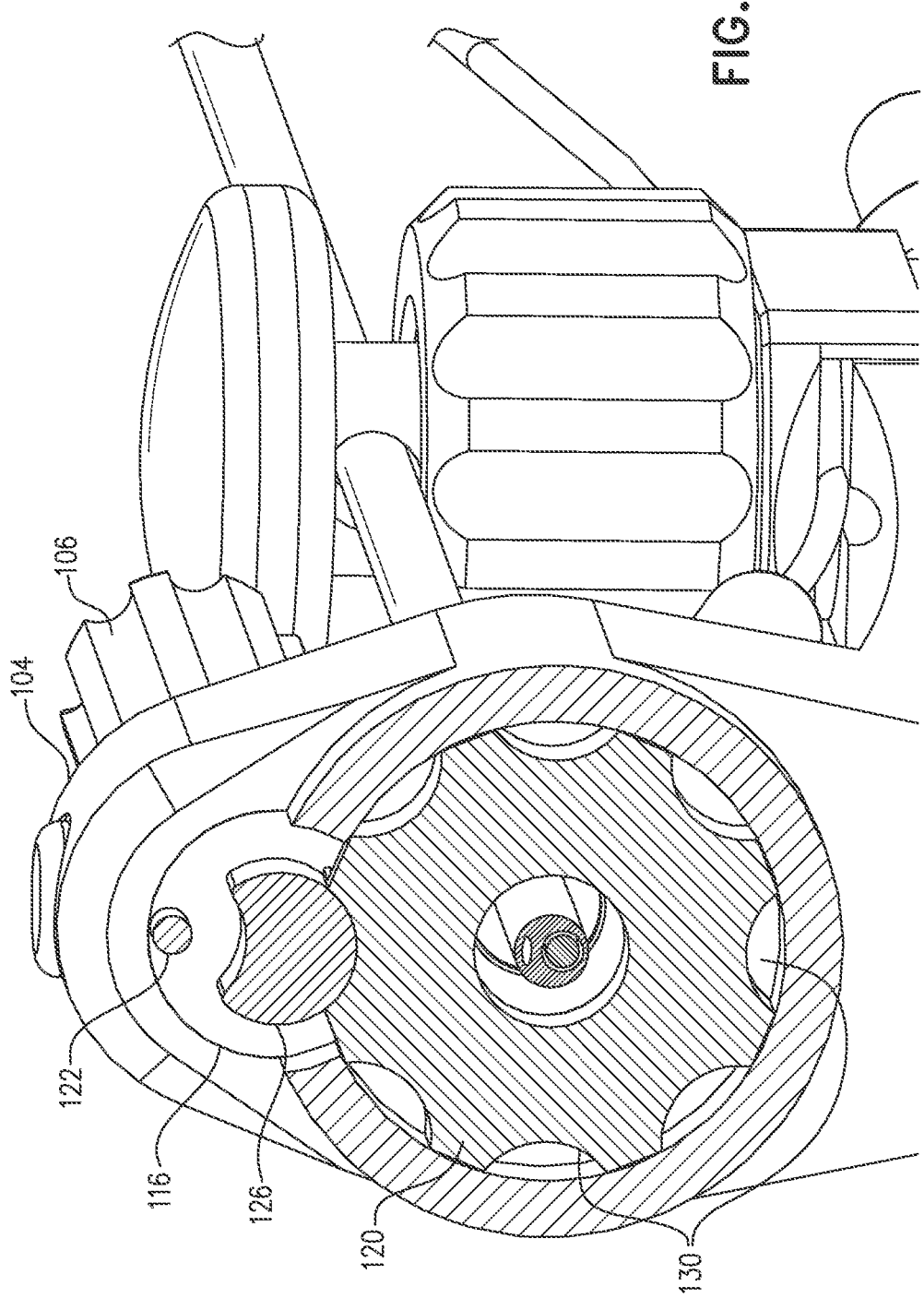
Figure 8:
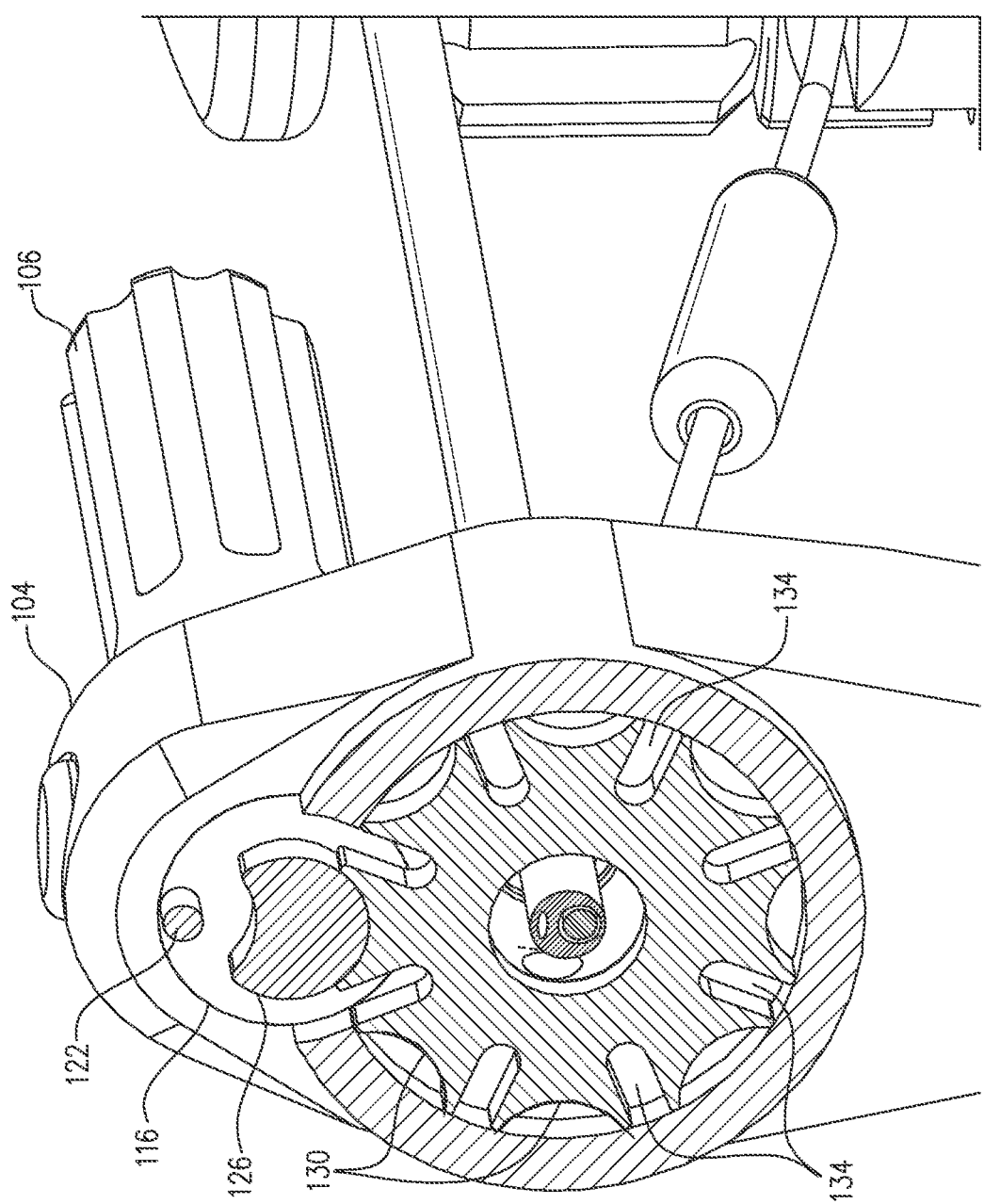
Figure 9:
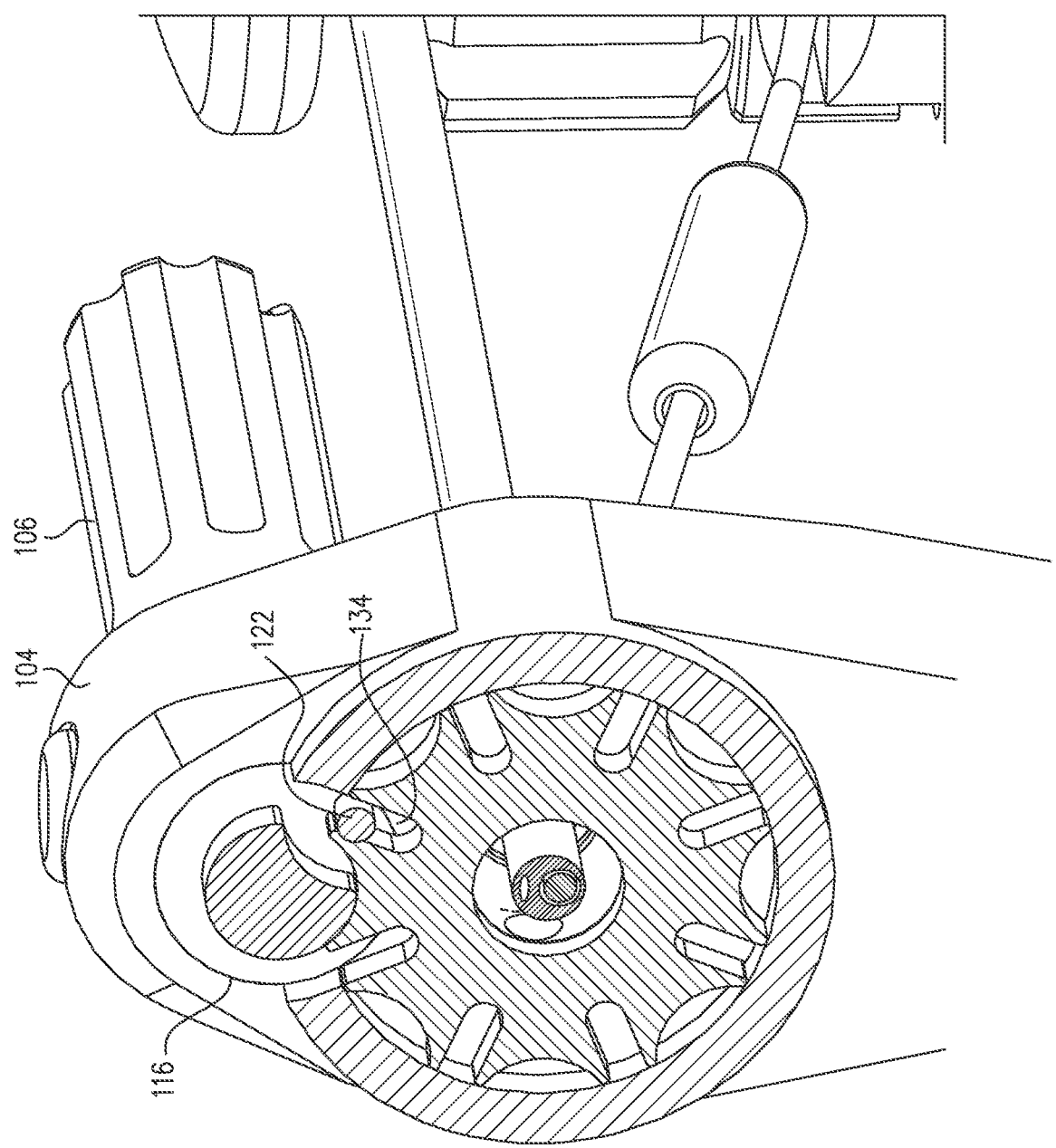

FIGS. 6, 7, 8, and 9 are schematic figures illustrating rotation system 109, according to an embodiment of the present invention. FIG. 6 illustrates a portion of the rotation system with enclosure 104 hidden. FIGS. 7, 8, and 9 illustrate portions of the rotation system with a part of enclosure 104 visible.

As illustrated in FIG. 6, rotation system 109 uses a Geneva drive 114, also termed a Geneva mechanism 114, to rotate tube 100 around axis 92. Knob 106 is fixedly attached to a drive wheel 116 of the mechanism, and the drive wheel mates with a driven wheel 120 of the mechanism. Driven wheel 120 is fixedly attached to the proximal end of tube 100 so that an axis of rotation of the driven wheel coincides with axis of symmetry 92, and so that as the driven wheel rotates, tube 100 rotates about its axis of symmetry.

As shown in FIGS. 7 and 8, drive wheel 116 comprises a pin 122, and a lune-shaped element 126. FIG. 7 illustrates driven wheel 120 as seen from tube 100, and FIG. 8 illustrates the internal construction of the driven wheel, showing indentations 130 and slots 134 of the driven wheel. During rotation of the Geneva drive, indentations 130 are engaged by lune-shaped element 126, and pin 122 engages and travels within slots 134. The engagement of pin 122 within a specific slot 134 is illustrated in FIG. 9.

Drive 114 translates continuous rotation of knob 106, typically implemented by a thumb and finger of the hand holding tool 21, into intermittent rotation of tube 100. It will be understood that while tube 100 is not being rotated, the engagement of lune-shaped element 126 with a specific indentation 130 locks tube 100 in place, so that the tube is prevented from inadvertent rotation.

By way of example, in the illustrated embodiment driven wheel 120 has eight different fixed positions, corresponding to the eight different indentations 130, but it will be understood that the scope of the present invention comprises Geneva drives with other numbers of different fixed positions. Typically all the different fixed positions and their respective different indentations are distributed symmetrically about the axis of rotation of the driven wheel.

It will be understood that continuous rotation of the rotatable knob 106 causes tube 100 to rotate about axis of symmetry 92 in discrete angular steps. Thus, for the eight different fixed positions illustrated, by way of example, in the figures, for driven wheel 120, tube 100 rotates to eight fixed positions, each fixed position separated from an adjacent fixed position by 45°. Once in one of the positions, tube 100 is effectively locked in place, regardless of rotation of knob 106, until the knob has rotated sufficiently to initiate transfer of the tube to an adjacent fixed position.

FIG. 10 and FIG. 11 are schematic illustrations of portions of guidewire 115 and balloon insertion mechanism 119, according to an embodiment of the present invention. In FIGS. 10 and 11 tube 100 has been hidden. FIG. 10 shows a balloon 150, in its nondilated state, that is attached at its proximal end to a distal end of an insertion rod 154 comprised in the mechanism. Balloon 150 is attached at its distal end to a balloon holding tube 160, and the tube is sealed at its proximal end to the distal tip of rod 154. Tube 160 is shown in a transparent form in FIG. 11.

Tube 160 permits the passage of guidewire 115 through a lumen of the tube, and the guidewire is inserted into the tube via a first channel 164 in rod 154. Channel 164 is also configured to transfer fluid, such as irrigation fluid, through the channel, so that the fluid exits from a distal end of tube 160.

Guidewire 115 may comprise a magnetic sensor 32A at its distal end. In some embodiments rod 154 may also comprise a magnetic sensor 32B at the distal end of the rod. The sensors enable physician 54 to track the guidewire and rod 154 after they have been inserted into patient 22.

In some embodiments the distal end of the guidewire is deflectable, typically by having wires (not shown in the figure) leading from the distal end to the proximal end, and adjustably tensioning the wires to form a desired deflection.

Rod 154 also comprises a second channel 170, that is used to convey air to the balloon so as to inflate the balloon. The channel may also be used to remove air so as to deflate the balloon.

FIG. 12 is a schematic transparent view of manifold 127, according to an embodiment of the present invention. Guidewire 115 is supported by the manifold, but is able to slide within it. A proximal end of rod 154 is fixed within the manifold and the manifold has channels connected to first channel 164 and second channel 170 (visible in FIGS. 10 and 11) of the rod, and respectively to a fluid supply tube 180 and an air supply tube 184.

Figure 13:
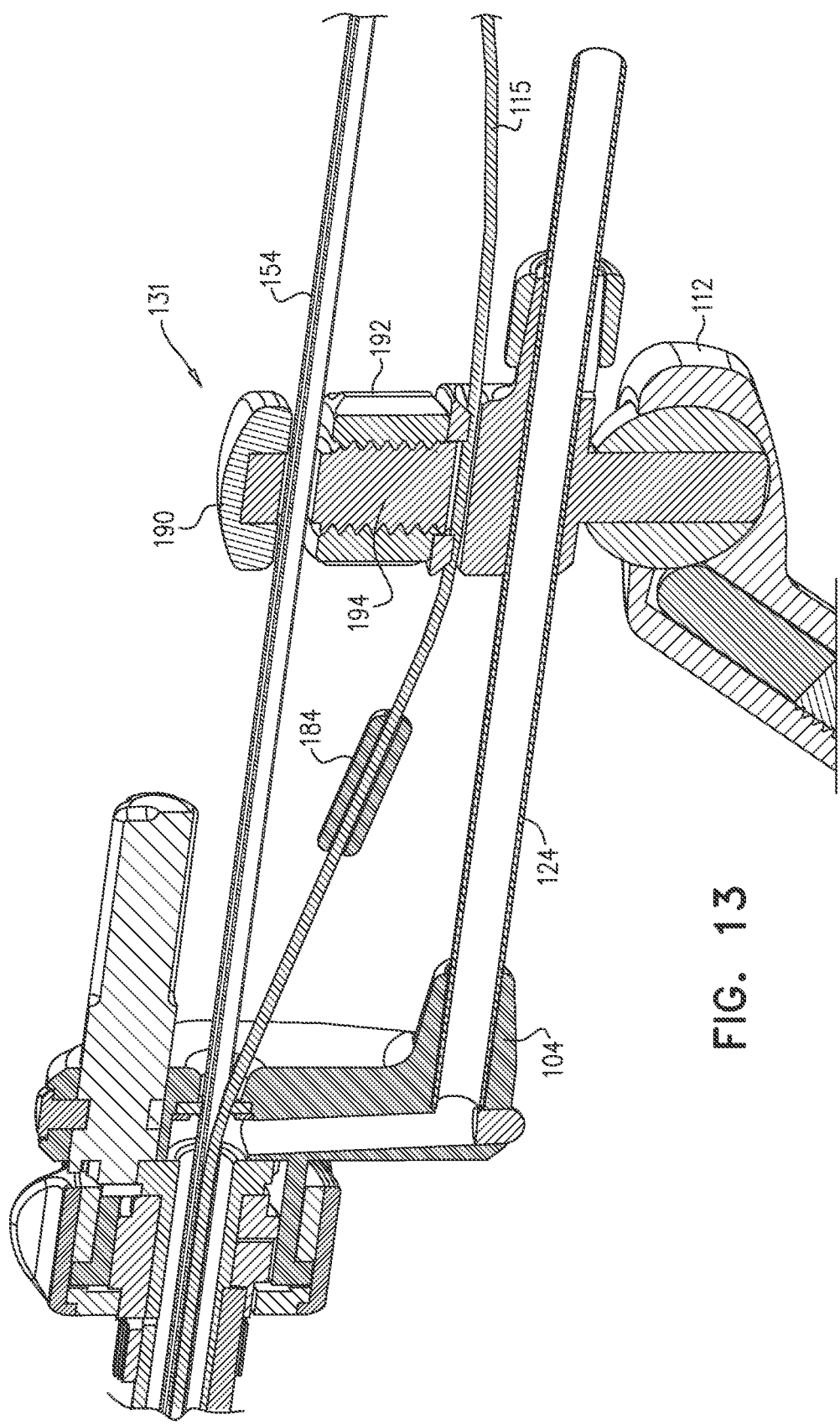
FIG. 13 is a schematic sectional view of a locking mechanism, according to an embodiment of the present invention.

FIG. 13 is a schematic sectional view of locking mechanism 131, according to an embodiment of the present invention. Mechanism 131 is mounted on ball-joint 112, and fixedly couples suction tube 124 to the handle. As shown in the figure, suction tube 124 provides a channel into enclosure 104, and so may be used by the physician for suction, thereby withdrawing material such as blood or mucus through tube 100 and the enclosure.

Rod 154 and guidewire 115 both traverse the mechanism, which comprises a nut 192 turning on a screwed section 194. In an unlocked state of the mechanism, when nut 192 is in the center of the screwed section, both the rod and the guidewire are free to move, proximally and distally, within the mechanism and thus within tube 100 of tool 21. Movement of rod 154 may be achieved by the physician pushing or pulling manifold 127. Movement of the guidewire may be achieved by the physician squeezing a sponge-like cylinder 184 surrounding the guidewire, so as to grip the guidewire, and then moving the gripped guidewire proximally or distally.

In a first locked state of the mechanism, which is implemented by the physician turning nut 192 of the mechanism in a first direction so as to raise the nut, rod 154 is fixedly held by the locking mechanism against knob 190 while guidewire 115 is free to move.

In a second locked state of the mechanism, which is implemented by the physician turning nut 192 in a second direction, opposite the first direction, so as to lower the nut, guidewire 115 is fixedly held by the locking mechanism while rod 154 is free to move.

During a typical sinuplasty procedure, physician 54 inserts tube 100 and section 84 into patient 22 so that the distal end of section 84 is in proximity to the sinuplasty site. Prior to, or during, the insertion, the physician may rotate tube 100 and/or deflect section 84, as described above, so as to best position the distal end of the section.

The physician may then use sponge-like cylinder 184 to thread guidewire 115 through channel 164 of rod 154, and through the lumen of tube 100, until it exits the distal end of section 84. The physician typically positions the guidewire so that its distal end is beyond the site that is set for sinuplasty.

With the guidewire in position, the physician may then slide the balloon insertion mechanism, i.e., rod 154, along the guidewire until the balloon of the mechanism reaches the desired location, at which stage the balloon may be locked in place by locking the balloon insertion mechanism with locking mechanism 131. Once in position, the balloon may be inflated, to achieve the sinuplasty, by passing air into channel 170.

Once the sinuplasty procedure has been performed, the guidewire and rod 154 may be withdrawn from the patient by reversing the steps above.

Although the embodiments described herein mainly address improvements in a tool for ENT, the methods and systems described herein may also be used in other, non-ENT applications, such as in neuro, gastric and other laparoscopic surgeries.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A balloon sinuplasty tool, comprising:
   an enclosure;
   a rotatable knob retained by, and protruding from, the enclosure;
   a tube having a proximal end retained by the enclosure, the tube having an axis of symmetry;
   a guidewire insertion tube configured to guide a guide wire therethrough and hold a balloon thereon,
   a balloon insertion mechanism; and
   a Geneva drive retained within the enclosure, the Geneva drive comprising a drive wheel fixedly attached to the rotatable knob and a driven wheel fixedly attached to the proximal end of the tube, so that an axis of rotation of the driven wheel coincides with the axis of symmetry of the tube,
   whereby a continuous rotation of the rotatable knob causes the tube to rotate about the axis of symmetry in discrete angular steps.

2. The tool according to claim 1, wherein the Geneva drive has eight different fixed positions.

3. The tool of claim 1, wherein the guidewire insertion tube is sealed at its proximal end to a distal tip of a rod and wherein the rod includes a first channel through which the guidewire is configured to be inserted into the guidewire insertion tube and a second channel configured to convey air to the balloon.

4. The tool of claim 1, further comprising a first magnetic sensor mounted on one of a distal end of the guide wire or on a distal end of the rod, wherein the first magnetic sensor is configured to track position in-vivo.

5. The tool of claim 4, further comprising a second magnetic sensor mounted on the other one of the distal end of the guide wire or the distal end of the rod, wherein the second magnetic sensor is configured to track position in-vivo.

6. A method, comprising:
   providing an enclosure;
   positioning a rotatable knob to be retained by, and protrude from, the enclosure;
   positioning a tube having a proximal end to be retained by the enclosure, the tube having an axis of symmetry;
   positioning a guidewire insertion tube, wherein the guidewire insertion tube is configured for guiding a guide wire therethrough and holding a balloon thereon,
   positioning a balloon insertion mechanism; and
   positioning a Geneva drive to be retained within the enclosure, the Geneva drive comprising a drive wheel fixedly attached to the rotatable knob and a driven wheel fixedly attached to the proximal end of the tube, so that an axis of rotation of the driven wheel coincides with the axis of symmetry of the tube,
   whereby a continuous rotation of the rotatable knob causes the tube to rotate about the axis of symmetry in discrete angular steps.

7. The method according to claim 6, wherein the Geneva drive has eight different fixed positions.

* * * * *